(12) United States Patent
Gros et al.

(10) Patent No.: US 7,531,066 B2
(45) Date of Patent: May 12, 2009

(54) METHOD FOR THE PURIFICATION OF ACROLEIN

(75) Inventors: Georges Gros, Antony (FR); Patrick Rey, Lyons (FR); Michel Garrait, Charly (FR)

(73) Assignee: Adisseo Ireland Ltd., Dublin (IE)

( * ) Notice: Subject to any disclaimer, the term of this patent is extended or adjusted under 35 U.S.C. 154(b) by 704 days.

(21) Appl. No.: 10/500,715

(22) PCT Filed: Feb. 12, 2003

(86) PCT No.: PCT/FR03/00454

§ 371 (c)(1),
(2), (4) Date: Nov. 5, 2004

(87) PCT Pub. No.: WO03/068721

PCT Pub. Date: Aug. 21, 2003

(65) Prior Publication Data

US 2005/0103616 A1    May 19, 2005

(30) Foreign Application Priority Data

Feb. 12, 2002   (FR)   ................... 02 01686

(51) Int. Cl.
*B01D 3/00*  (2006.01)
*C07C 47/22* (2006.01)
*C07C 45/82* (2006.01)

(52) U.S. Cl. ............... 203/17; 203/2; 203/98; 568/458; 568/492

(58) Field of Classification Search .............. 203/2, 203/17, 98; 568/458, 492
See application file for complete search history.

(56) References Cited

U.S. PATENT DOCUMENTS

| | | | |
|---|---|---|---|
| 3,433,840 A * | 3/1969 | Yoshitsugu et al. | ......... 568/492 |
| 4,225,516 A | 9/1980 | Biola et al. | |
| 4,319,047 A | 3/1982 | Komorn et al. | |
| 5,352,837 A | 10/1994 | Hsu et al. | |
| 5,770,021 A * | 6/1998 | Hego et al. | ............... 203/8 |

FOREIGN PATENT DOCUMENTS

| FR | 2 460 925 | 1/1981 |
|---|---|---|
| FR | 2 735 989 | 1/1997 |

* cited by examiner

*Primary Examiner*—Virginia Manoharan
(74) *Attorney, Agent, or Firm*—Oliff & Berridge, PLC

(57) ABSTRACT

A process for purifying an aqueous solution to obtain purified gaseous acrolein by introducing the aqueous solution into a distillation column equipped at its base with at least one boiler and at its top with at least one condenser, withdrawing a liquid mixture essentially containing water at the base of the distillation column, withdrawing a gas essentially containing acrolein and water at the top of the distillation column, cooling the gas mixture withdrawn at the top of the distillation column in the condenser, to a temperature which makes it possible to obtain, on the one hand, an aqueous condensate and, on the other hand, an acrolein-rich gas mixture, and withdrawing the acrolein-rich gas mixture.

17 Claims, 2 Drawing Sheets

METHOD FOR THE PURIFICATION OF ACROLEIN

Figure 1:
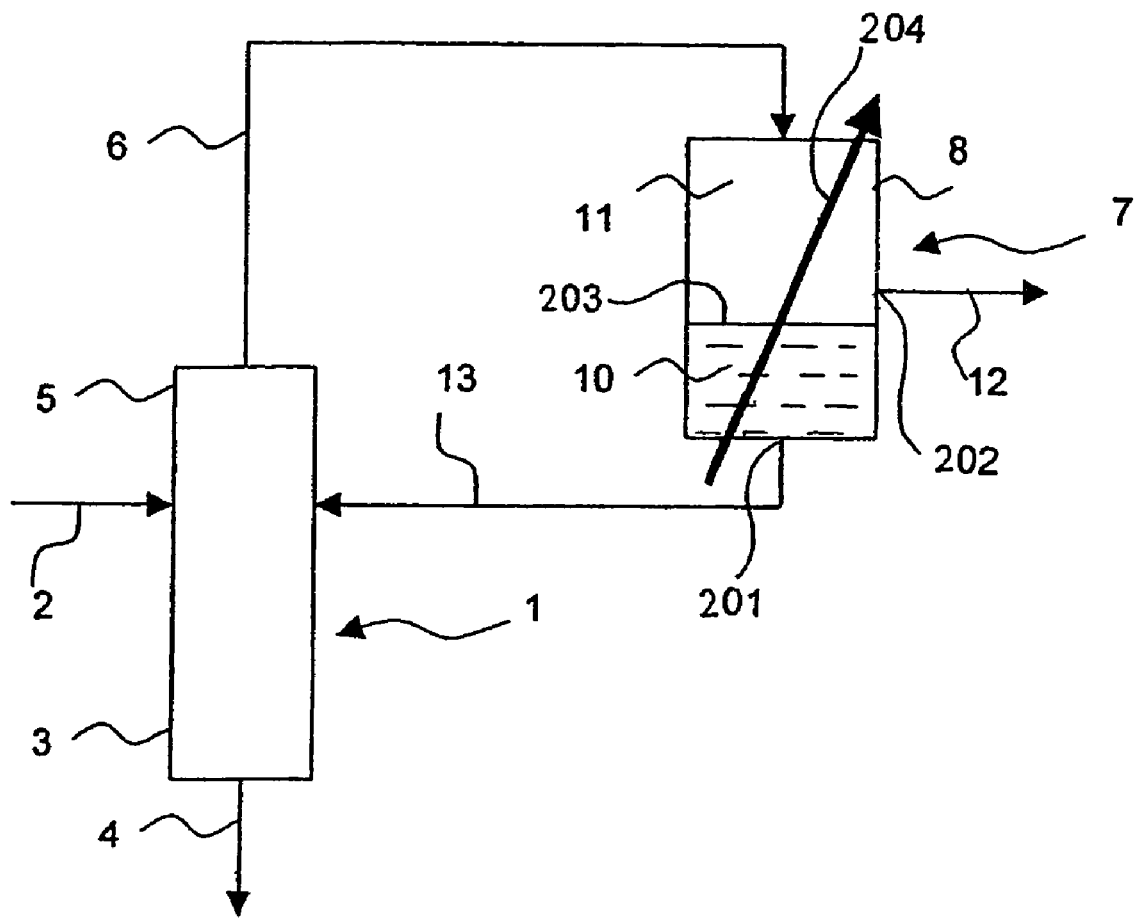

The field of the present invention is that of the manufacture of acrolein as intermediate product or final product. It relates in particular to the purification of acrolein from an aqueous acrolein phase. The invention also relates to the field of the manufacture of MTPA, that is to say of 3-(methylthio)propionaldehyde.

Acrolein is a starting material, a major use of which on the industrial scale is the synthesis of MTPA by reaction of acrolein with methyl mercaptan.

The processes in which acrolein is manufactured are well known. These processes generally comprise a propylene and/or propane oxidation reaction stage. A crude gaseous acrolein-based product can thus be obtained. This crude product generally exists in the form of a gas mixture comprising, first, acrolein in a proportion generally of greater than 10% by weight, secondly, inert or noncondensable gases (also known as offgases), such as nitrogen, oxygen, carbon monoxide, carbon dioxide, propylene or propane, thirdly, water and, fourthly, reaction byproducts, such as acids, aldehydes, alcohols and other compounds. Subsequent treatments are therefore necessary to remove some of the compounds from the crude product and to isolate purified acrolein.

The crude acrolein-based product is generally subjected to a first treatment which makes it possible to remove acids, such as acrylic acid and acetic acid. A second treatment subsequently makes it possible to absorb the acrolein in water using an absorption column, at the bottom of which an aqueous acrolein solution is collected. This solution is subsequently subjected to a purification stage using one or more distillation columns to isolate purified acrolein in the gaseous form.

The purification of the acrolein often requires the use of two distillation columns. The first optional column makes it possible to deoxygenate the solution and removes the light impurities. The second column is, for its part, operated so as to obtain, at the top of said column and in particular at the outlet of the condenser, liquid acrolein in an azeotropic concentration with water.

Whether with one or more distillation columns, fouling of these columns constitutes a problem often encountered during purification of acrolein. This fouling is often characterized by the deposition of a solid phase resulting from the polymerization of the acrylic acid residues, indeed even of acrolein. In the specific case of purification processes using two columns, these fouling deposits generally occur in the second column, which, furthermore, is often used under azeotropic conditions.

These depositions bring about a gradual decline in the efficiency of the distillation and result in partial, indeed even complete, blocking of the distillation column. This problem thus necessitates frequent shutdowns of plants for the production of acrolein in order to carry out the maintenance operations which are necessary to remove the deposits in the distillation column or columns. These shutdowns thus result in high costs and in a consequent loss in the capacity of the production plants.

The present invention is thus targeted at a process for purifying acrolein in a simple, inexpensive and safer way while minimizing the fouling deposits in the distillation column used.

It has thus been found that it is possible to overcome the disadvantages related to fouling by distilling an aqueous acrolein solution under specific operating conditions.

A subject matter of the present invention is thus a continuous process for the purification of acrolein, in which:

an aqueous acrolein solution, devoid of gas which is difficult to condense, is fed to a distillation column equipped at its base with at least one boiler and at its top with at least one condenser, a liquid mixture essentially comprising water is withdrawn at the base of the distillation column, a gas mixture essentially comprising acrolein and water is withdrawn at the top of the distillation column, the gas mixture withdrawn at the top of the distillation column is cooled, in the condenser, to a temperature which makes it possible to obtain, on the one hand, an aqueous condensate and, on the other hand, a substantial amount of an acrolein-rich gas mixture, and purified acrolein is withdrawn from the acrolein-rich gas mixture.

More specifically, the invention relates to a continuous process for the purification of acrolein, in which:

an aqueous acrolein solution is introduced into a distillation column equipped at its base with at least one boiler and at its top with at least one condenser, a liquid mixture comprising water is withdrawn at the base of the distillation column, a gas mixture comprising acrolein is withdrawn at the top of the distillation column, the gas mixture withdrawn at the top of the distillation column is cooled, in the condenser, to a temperature which makes it possible to obtain, on the one hand, an aqueous condensate and, on the other hand, an acrolein-rich gas mixture, and said gas mixture is withdrawn, characterized in that the distillation is determined in order to obtain, at the base of the column, a nonazeotropic liquid mixture essentially comprising water and the condensation is determined in order to obtain an aqueous condensate substantially depleted in acrolein and a gas mixture substantially enriched in acrolein.

Preferably, the gas mixture obtained at the column top comprises, by volume, between 30% and 70% and preferably between 40% and 60% of water.

By virtue of the abovementioned operating choices, the distillation is carried out at temperatures which remain limited since in particular the production at the column top of a gas mixture comprising a not insignificant proportion of water is accepted. The separation of the water is subsequently obtained by specific conditions of cooling in the condenser, compensating as it were for the limited separation of the acrolein in the distillation column.

Another subject matter of the present invention is a continuous process and a plant for the manufacture of MTPA, that is to say of 3-(methylthio)propionaldehyde.

The processes for the manufacture of MTPA of the prior art generally involve a chemical reaction of liquid acrolein with methyl mercaptan generally in the presence of a catalyst. These processes often require one or more intermediate storages of liquid acrolein. This can present a safety problem related to the characteristics of acrolein, in particular its polymerization, its high toxicity and its flammability.

Other processes have been developed in order to respond to this safety problem, for example in U.S. Pat. Nos. 4,225,516, 4,319,047 and 5,352,837.

They disclose a partial purification of the crude gas mixture comprising acrolein, for example by two successive cooling operations, to remove in particular the acids. The gas stream thus purified, comprising only a limited amount of acrolein diluted in the offgases from the reaction, is reacted with MSH in a reactor by gas-liquid contact.

In this case, the offgases are removed subsequent to the reaction between acrolein and MSH; they result in a substantial loss of acrolein and MTPA by stripping or elution. Furthermore, the offgases comprising these acrolein and MTPA fractions require specific and expensive treatments in order to eliminate the smells and to comply with legislation relating to discharges.

In order to respond, on the one hand, to the safety problem related to the storage of liquid acrolein and, on the other hand, in order to avoid losses in yield by stripping of the MTPA and the expensive treatment of the gaseous effluent, it has been found that it is advantageous to carry out the process for the purification of acrolein described above and to manufacture MTPA by reacting the gaseous acrolein thus purified, obtained by said process, directly with liquid or gaseous methyl mercaptan. Thus, the reaction for the manufacture of MTPA can be carried out directly starting from purified gaseous acrolein devoid of "noncondensable" gases. This method of operation thus makes it possible to eliminate any intermediate storage of liquid acrolein, thus solves the safety problem mentioned above, and losses of MTPA and of acrolein.

The present invention is thus targeted at a continuous process and at a plant for the manufacture of MTPA comprising a stage of purification of acrolein according to the process for the purification of acrolein described above.

The present invention relates in particular to a continuous process for the manufacture of MTPA, characterized in that:
(a) a vapor-phase oxidation of propylene is carried out using a catalyst, so as to obtain a crude acrolein-based product,
(b) acids present in the crude product obtained in the preceding stage are removed,
(c) the product obtained in the preceding stage is absorbed with water, so as to obtain an aqueous acrolein solution substantially devoid of acids,
(d) said solution is purified, so as to obtain purified gaseous acrolein, and
(e) the purified gaseous acrolein obtained in the preceding stage is reacted with MSH, that is to say methyl mercaptan, so as to obtain MTPA, and the "noncondensable" gases originally present in the crude product resulting from oxidation stage (a) are separated before stage (e).

Preferably, the separation of the "noncondensable" gases is carried out before purification stage (d), in particular during stage (b) and/or stage (c), for example during stage (c).

The "noncondensable" gases are either recycled to oxidation stage (a) or discharged from the process and, for example, incinerated at a relatively low temperature (900° C., for example), as regards carbonaceous discharges and not sulfurous discharges.

The determining advantage of a separation of the "noncondensable" gases upstream of the synthesis of MTPA is that said gases do not comprise any sulfur compound generated by MSH and/or MTPA and can therefore be recycled to the oxidation of propylene, as a mixture with the latter, without the risk of poisoning the oxidation catalyst with sulfur compounds.

The separation of the "noncondensable" gases upstream of the purification of the acrolein also makes it possible to remove a gas ballast, normally in a relatively high proportion by volume, throughout the process resulting in MTPA.

By virtue of this upstream separation of the "noncondensable" gases, there is no cause to carry it out during or subsequent to the synthesis of MTPA by reaction between acrolein and MSH, which prevents having to remove sulfur compounds before discharge by incineration of the offgases at a relatively high temperature (1200° C., for example).

In the event of recycling of the noncondensable gases to the oxidation, the MTPA yield, expressed with respect to the incoming molar amount of propylene, is found to be substantially improved.

The present invention also relates to a continuous process for the manufacture of MTPA, characterized in that:
(a) a vapor-phase oxidation of propylene is carried out using a catalyst, so as to obtain a crude acrolein-based product,
(b) acids present in the crude product obtained in the preceding stage are removed,
(c) the product obtained in the preceding stage is absorbed with water, so as to obtain an aqueous acrolein solution separated from the "noncondensable" gases,
(d) said solution is purified, so as to obtain purified gaseous acrolein, and
(e) the purified gaseous acrolein obtained in the preceding stage is reacted directly with liquid or gaseous MSH, that is to say methyl mercaptan, so as to obtain MTPA.

Preferably, stage (e) is carried out between liquid MSH and purified acrolein maintained in the gas phase.

Figure 2:
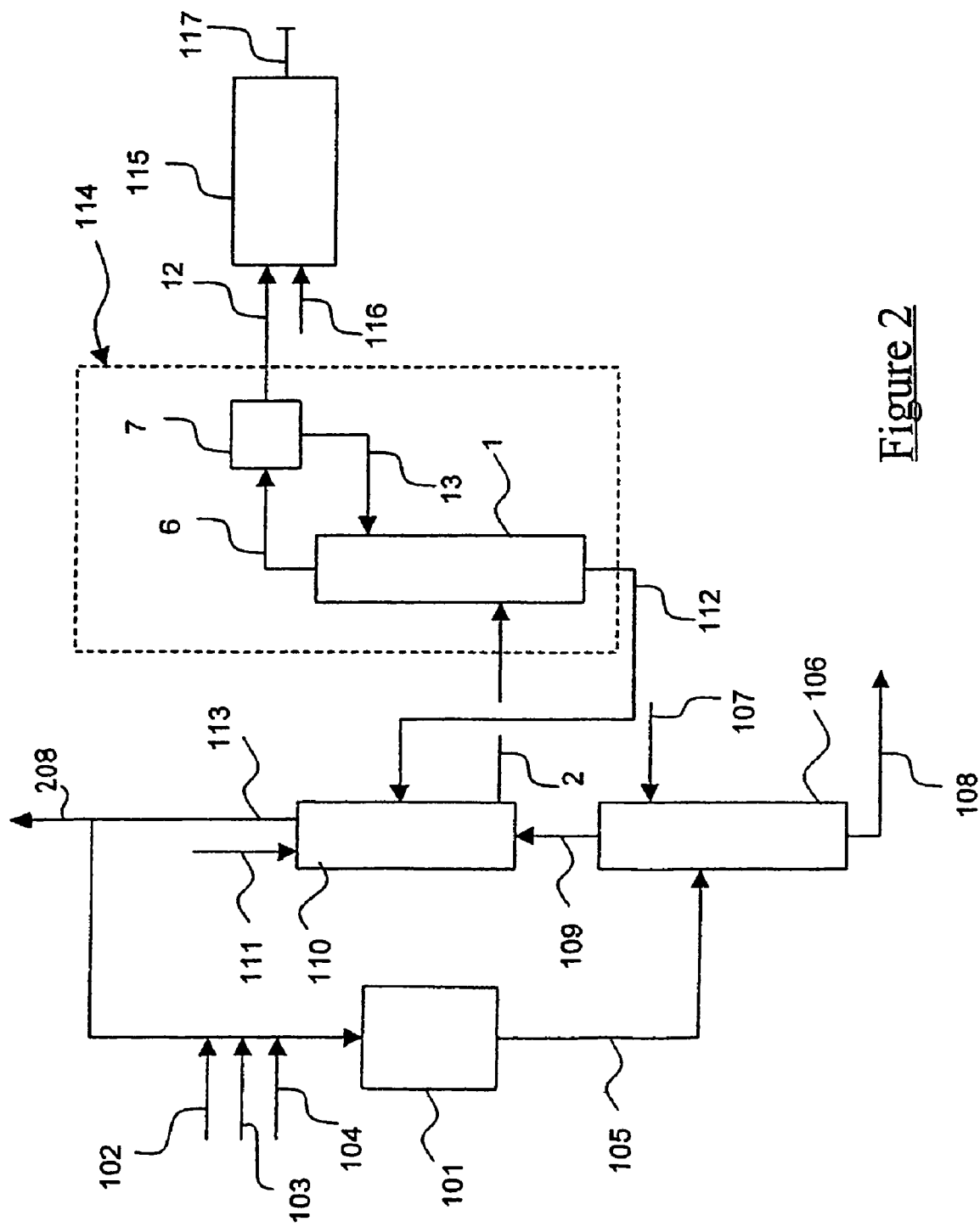

FIGS. 1 and 2 represent, without implied limitation, a device for the purification of acrolein and a plant for the manufacture of MTPA employing the process of the invention.

FIG. 1 diagrammatically illustrates a device for the purification of acrolein according to the invention.

FIG. 2 diagrammatically illustrates a plant for the manufacture of MTPA according to the invention.

The present invention is described in more detail subsequently with reference to FIG. 1.

The process of the invention is carried out by distillation of an aqueous acrolein solution 2 devoid of "noncondensable" gases, that is to say a mixture in the liquid form essentially comprising acrolein and water.

The term "noncondensable" gases or "inert" gases or "offgases" is understood to mean any gas which cannot be condensed, relatively, under the purification conditions according to the process of the invention. These gases can generally only be condensed at temperatures well below 100° C. By way of examples, these "noncondensable" gases can be nitrogen, propylene, propane or oxygen, which are generally present in the gas stream resulting from the synthesis of acrolein.

The "noncondensable" gases were removed in the process according to the invention during a preliminary stage of absorption of the acrolein in water.

The aqueous acrolein solution 2, that is to say the feed mixture for the distillation column, can have a concentration of acrolein of greater than 1% and in any case of less than or equal to a concentration corresponding to the solubility limit of acrolein in water.

The aqueous acrolein solution 2 preferably has a concentration of acrolein of less than or equal to the solubility limit of acrolein in water, for example 5% by weight.

The distillation column 1 is also equipped at its base with a boiler (not represented) having the function of at least partially evaporating the aqueous solution obtained at the column bottom. The operating conditions of the boiler are conventional. The temperature in the boiler can be maintained, in the case of a distillation column operated at atmospheric pressure, at a value ranging from 100 to 130° C., preferably from 100 to 120° C., especially from 102 to 110° C. A person skilled in the art will know how to adjust these temperature conditions according to whether the operation is carried out under vacuum or under pressure.

According to the invention, a mixture 4 essentially comprising water is withdrawn at the base of the distillation column 1. This withdrawn mixture can nevertheless have an acrolein concentration of less than 0.1% by weight, preferably of less than 0.05% by weight, especially of less than 0.01% by weight.

According to the present invention, the aqueous acrolein solution 2 is purified in a distillation column 1, at the top of which is withdrawn a gas mixture 6 essentially comprising acrolein and water. This gas mixture 6 is subsequently, in a first step, cooled by means represented diagrammatically by the reference 204, so as to obtain a condensate 10 and a substantial amount of an acrolein-rich gas mixture 11. In a second step, purified acrolein 12 in the gaseous form is withdrawn from the acrolein-rich gas mixture 11. The cooling of the mixture 6 withdrawn at the column top and the withdrawing of the purified acrolein 12 constitute two essential stages of the process of the invention, it being possible for these stages to occur simultaneously or consecutively.

According to one of these essential aspects, the mixture 6 withdrawn at the top of the distillation column is thus cooled in a condenser 7, so as to obtain the condensate 10 and a substantial amount of an acrolein-rich gas mixture 11.

The term "substantial amount" is understood to mean that the acrolein is found, by virtue of the cooling conditions selected, largely in the acrolein-rich gas mixture 11, rather than in the condensate 10. It may be considered that more than 50%, preferably more than 70%, especially more than 90%, of the amount by weight of acrolein initially present in the gas mixture 6 withdrawn at the top of column 1 is found, after cooling 204, purified in the gaseous form.

Such an acrolein-rich gas mixture can be obtained by a judicious choice of the temperature of cooling 204 of the condenser 7. The choice of this temperature must obviously be made by taking into account the value of other physical parameters, such as, for example, the pressure.

Thus, according to a specific form of the present invention, if the distillation column 1 is maintained at a pressure P, the temperature in the condenser 7 must be maintained at a value T according to the equation $T>21.28*P+32.9$, P being expressed in atmospheres. For example, if P is 1 atm, T is $>53°$ C., P is 2 atm, T is $>75°$ C.

The column 1 is advantageously maintained at atmospheric pressure, which requires maintaining a temperature in the condenser 7 at a value of greater than 54° C., preferably ranging from 55 to 70° C., especially ranging from 60 to 65° C.

According to another essential aspect, the purified acrolein 12 is withdrawn from the acrolein-rich gas mixture 11, the latter having been obtained by cooling 204 of the gas mixture 6 withdrawn at the top of distillation column 1.

The verb "to withdraw" is to be understood in a very general way. According to the invention, the term "to withdraw a product from a mixture" is understood to mean the fact of fractionating or of removing at least a portion of said mixture.

Preferably, the purified acrolein 12 is obtained by withdrawing all the acrolein-rich gas mixture 11. In this case, the purified acrolein can be isolated by simple separation of the acrolein-rich gas mixture 11, on the one hand, and of the condensate 10, on the other hand. The purified acrolein 12 can subsequently be withdrawn via a pipe emerging in the upper part of the condenser 7 comprising the acrolein-rich gas mixture 11.

The purified acrolein 12 generally exists in the form of a gas mixture essentially comprising acrolein with a low water content. The purification relates mainly to a significant reduction in the water content.

Advantageously, by way of example, by adjusting the condensation temperature, the purified acrolein 12 can have an acrolein concentration ranging from 86 to 95% by weight, preferably from 88 to 94% by weight, especially from 90 to 93% by weight.

According to an advantageous form of the present invention, the condensate 10 is at least partially reintroduced 13 into the distillation column. Preferably, all of the condensate is reintroduced at the top of the distillation column 1.

In order to even further reduce fouling deposits, the acrolein solution 2 can advantageously be subjected to a preliminary deoxygenation stage before being fed to the distillation column 1. This deoxygenation can be carried out by placing the acrolein solution 2 under vacuum.

Likewise, it is possible to envisage using a distillation column 1 having downcomerless plates with large perforations and having heated walls, so as to avoid the condensation of still liquid which can initiate undesirable points of polymerization. However, this possibility may prove to be expensive and unnecessary, in view of the improvements introduced by the process of the present invention.

The advantages of the purification process according to the present invention are to make it possible:

to obtain acrolein in the gas phase 12 with a high degree of purity, without requiring shutdowns of the plant to remove fouling deposits from the column 1 and the condenser 7 as a result of the polymerization of acrylic acid and/or of acrolein, to minimize the frigorie requirements in the condenser 7, to avoid the need for storage of liquid acrolein and thus to make it possible to minimize the intermediate stocks of this highly toxic, inflammable and dangerous product.

With reference to FIG. 2, another subject matter of the present invention is a continuous process for the manufacture of MTPA, that is to say 3-(methylthio)propionaldehyde. This process is characterized in that it comprises a stage 114 of purification of the acrolein according to the process described above.

MTPA is an intermediate product in the manufacture of methionine or HMBA, that is to say 2-hydroxy-4-(methylthio)butanoic acid. Methionine is an essential amino acid which makes it possible to supplement deficiencies in the diet of animals. HMBA provides a source of methionine which is commonly used as a methionine supplement in the formulation of animal feed. MTPA is commonly required for the manufacture of HMBA or of methionine.

According to a preferred form of the invention, with reference to FIG. 2, the continuous process for the manufacture of MTPA is characterized in that:

(a) a vapor-phase oxidation 101 of propylene 104 is carried out using a catalyst, so as to obtain a crude acrolein-based gaseous product 105, (b) acids present in the crude product 105 obtained in the preceding stage are removed 106, (c) the product obtained in the preceding stage is absorbed 110 with water 111, so as to obtain an aqueous acrolein solution 2 which is substantially devoid of acids and which is separated from the "noncondensable" gases 113, (d) said solution 2 is purified by virtue of the process 114 for the purification of acrolein described above, so as to obtain a stream 12 of purified gaseous acrolein, and (e) the purified gaseous acrolein 12 obtained in the preceding stage is reacted with gaseous or liquid MSH 116, that is to say methyl mercaptan, in the presence of a catalyst, so as to obtain MTPA 117.

The crude acrolein-based product 105 obtained in the first stage (a) of the process for the manufacture of MTPA generally exists in the form of a gas mixture comprising, firstly, acrolein in a proportion of greater than 5%, preferably 10%, secondly, noncondensable gases, such as nitrogen, oxygen, carbon monoxide, carbon dioxide, propane or propylene, thirdly, water and, fourthly, reaction byproducts, such as acids, aldehydes, alcohols and other compounds.

This crude product 105 is subsequently treated, during a second stage (b), so as to remove acids, such as, for example, acrylic acid and acetic acid, by any means.

The crude product thus treated 109 can, according to stage (c) of the process, be brought into contact with cooled water 111 in an absorption column 110, in order to collect an aqueous acrolein solution 2 at the base of said column and an offgas stream 113, comprising only traces of acrolein, at the top. The noncondensable gases 113 can be entirely removed via the pipe 208 or can be partially recycled to the process 101 for the oxidation of propylene 104.

The fourth stage (d) of the process for the manufacture of MTPA consists in purifying the aqueous acrolein solution 2 according to the purification process 114 described above. According to this purification process, in a first step, a distillation column 1 is fed with an aqueous acrolein solution 2 which is devoid of noncondensable gases or offgases.

As regards the fifth stage (e) of the process for the manufacture of MTPA, that is to say the reaction of purified acrolein 12 with MSH 116, the use may be envisaged of acrolein in the liquid or gaseous form in the presence of a catalyst.

According to an advantageous form of the present invention, the synthesis of MTPA is carried out between liquid MSH 116 or gaseous MSH 116 and purified acrolein 12 maintained in the gas phase. The advantage of this form lies in the simplification of the process and in particular in the fact of avoiding intermediate storages of liquid acrolein which would be harmful in terms of safety.

One advantage of the present invention is to make possible the synthesis of MTPA using a source of purified acrolein maintained in the gaseous form.

Another advantage of this novel process, which uses acrolein in the gaseous form but devoid of noncondensable gases, is to avoid, subsequent to the synthesis of the MTPA, the entrainment of sulfur compounds and of acrolein, which requires an expensive treatment and results in substantial losses in yield.

Another subject matter of the present invention is a device for the purification of acrolein comprising
a feed pipe for an aqueous acrolein solution 2 devoid of noncondensable gases,
a distillation column 1 fed via the feed pipe,
a withdrawal pipe 6 at the top of the distillation column 1,
a condenser 7 fed via the withdrawal pipe and equipped with a cooling means 204, in order to maintain the temperature at values which make it possible to obtain a condensate 10 and a substantial amount of an acrolein-rich gas mixture 11, and
a pipe 12 for discharge from the condenser 7 which makes it possible to isolate purified acrolein in the acrolein-rich gas mixture.

The condenser 7 is preferably vertical, in order to make possible flow by runoff along these internal walls. The condenser 7 is in particular equipped:

with an orifice 201 for discharge of the condensate 10 situated below a level 203 of condensate accumulated at the base of the condenser 7,
with an orifice 202 for discharge of the purified acrolein in the gaseous form situated above said level 203 of condensate, and
with two discharge pipes 13 and 12 connected to each of said orifices.

The invention also relates to a plant for the manufacture of MTPA comprising:
a reactor 101 which makes it possible to obtain a crude acrolein-based gaseous product 105,
a device 106 for removing acids, fed by virtue of a feed pipe 105 for crude acrolein-based gaseous product,
a device 110 for absorption of acrolein with water, fed by virtue of a feed pipe 109 for crude acrolein-based gaseous product devoid of acids,
a device 114 for the purification of acrolein fed by virtue of a feed pipe 2 with an aqueous acrolein solution, and
a reactor 115 for the manufacture of MTPA fed by virtue of a feed pipe 12 for purified acrolein and a feed pipe 116 for MSH, characterized in that the device 114 for the purification of acrolein is in accordance with that described above with reference to FIG. 1.

Preferably, the feed pipe 12 of the reactor 115 for the manufacture of MTPA is connected directly to the discharge pipe of the condenser 7 of the purification process.

FIG. 1 illustrates, diagrammatically and without implied limitation, a plant for the purification of acrolein in accordance with the present invention.

This plant comprises a distillation column 1 fed with an aqueous acrolein solution via a feed pipe 2. The distillation column 1 comprises a base 3 equipped with a boiler not represented in the figure. A mixture essentially comprising water is withdrawn from this base 3 via a withdrawal pipe 4. The distillation column comprises a top 5 which is connected to a withdrawal pipe 6.

The plant represented in FIG. 1 also comprises a condenser 7, the latter being fed via the withdrawal pipe 6 positioned at the top 5 of the distillation column 1. The condenser 7 is represented diagrammatically by a chamber 8 and by a pipe 204 (represented by an arrow) intended for the circulation of a liquid coolant. The chamber 8 in the condenser 7 comprises, in its lower part, the condensate 10 and, in its upper part, the acrolein-rich gas mixture 11. The condenser 7 is also connected to a pipe 12 for discharge of purified acrolein in the gaseous form. This pipe 12 emerges inside the upper part of the chamber 8 comprising the acrolein-rich gas mixture.

The purification plant represented in FIG. 1 also comprises a pipe 13 which makes possible the recycling to the distillation column of the condensate 10 accumulated at the bottom of the chamber 8 of the condenser 7.

FIG. 2 illustrates, diagrammatically and without implied limitation, a plant for the manufacture of MTPA in accordance with the present invention.

The plant comprises a reactor for the manufacture of crude acrolein 101 fed with propylene or propane, with air and with water via pipes represented respectively under the references 102, 103 and 104. A crude acrolein-based gaseous product is obtained in the reactor 101 by catalytic oxidation of propylene or propane by air in the presence of water. A pipe 105 connected to the reactor 101 makes it possible to transfer said crude product to the device 106 for removing the acids.

This device 106 for removing the acids is composed of a column for absorption with water which is fed, on the one hand, with crude acrolein-based gaseous product via the pipe 105 and, on the other hand, with water via a pipe 107. A liquid effluent comprising acids is discharged at the base of this column via a discharge pipe 108. At the top of the absorption column 106, a gaseous effluent comprising acrolein and devoid of acid is transferred via a pipe 109 to a device 110 for absorption of acrolein.

This device 110 for absorption of acrolein is also a column for absorption with water which is fed with crude acrolein-based gaseous product devoid of acid via the pipe 109 and with water via the pipes 111 and 112. The gaseous effluents obtained at the top of the device 110 can be partially recycled to the reactor 104 for the manufacture of acrolein via a pipe 113. An acrolein solution essentially comprising acrolein and water is transferred at the base of the absorption column 110 by virtue of the feed pipe 2 to a plant 114 for the purification of acrolein in accordance with that represented and described with reference to FIG. 1.

The purification plant 114 represented in FIG. 2 thus comprises, as described above:
- the feed pipe 2 for aqueous acrolein solution,
- the distillation column 1 connected to said pipe 2,
- the condenser 7 connected to the top of the distillation column 1 via the withdrawal pipe 6 and equipped with a cooling means (not represented), in order to maintain the temperature at values which make it possible to obtain a condensate and an acrolein-rich gas mixture,
- a discharge pipe 12 for purified acrolein in the gaseous form, isolated in the acrolein-rich gas mixture present in the condenser 7, and
- a pipe 13 which makes it possible for the recycling of the condensate to the distillation column 1.

The plant for the manufacture of MTPA represented in FIG. 2 also comprises a reactor 115 for the manufacture of MTPA equipped with a feed pipe for purified gaseous acrolein, said pipe corresponding to the discharge pipe 12. The reactor 115 is also fed via a feed pipe for MSH 116. The MTPA produced is discharged via a discharge pipe 117.

The following examples make it possible to understand the advantage of the present invention.

EXAMPLE 1

This example illustrates a process for the purification of acrolein of the prior art for which a single 40-plate distillation column is used. This column, maintained at atmospheric pressure, was fed with an acrolein solution comprising 6% by weight of acrolein and 93.5% by weight of water. The temperature at the base of this column was maintained at a value of 110° C. by virtue of a boiler. An azeotropic mixture of acrolein and of water was withdrawn at the top of this column and was completely condensed via a condenser. The mixture had an acrolein concentration of 95% by weight, the impurities being mainly composed of water, at a level of 3%, and of acetaldehyde, at a level of 1.5%. The nominal production of acrolein thus purified was 70 tonnes per day.

The column operated with these operating conditions for approximately 3 to 4 weeks at its nominal level of production. This column subsequently had to be shut down to clean the plates and the heat exchangers associated with this column.

EXAMPLE 1a

With the aim of minimizing the fouling deposits in the column used in example 1, the plant comprising it was modified by the addition of degassing under vacuum (20° C., 0.7 bar). This modification did not make it possible to significantly minimize the fouling deposits observed above.

EXAMPLE 2

This example illustrates a process for the purification of acrolein incorporated in a pilot-scale unit for the manufacture of MTPA according to the present invention.

Synthesis of Acrolein

A crude acrolein-based product 105 is produced at the outlet of a reactor 101 for the oxidation of propylene to acrolein in the vapor phase. This crude product was composed of a gas mixture having a temperature of 180° C. and comprising 63% by weight of noncondensable gases (propane, nitrogen, oxygen, propylene, CO, $CO_2$), 21% by weight of water, 12% by weight of acrolein, 2% by weight of acrylic acid and 2% of other compounds.

Absorption of the Acids

This crude acrolein-based product, in the vapor phase, was introduced 105 at the rate of 20 kg/h at the bottom of a cooling column 106, equipped with sieve plates, maintained at a pressure of 121 000 Pa. A cooled liquid 108 comprising acids and 1.3% by weight of acrolein was withdrawn at the bottom of the column and maintained at a temperature of 70.3° C. An acidic gas phase is withdrawn at the column top and subsequently cooled to 4° C.

Absorption of Acrolein

The acidic gas phase thus obtained was subsequently introduced with a flow rate of 16.2 kg/h at the base of a column 110 for absorption with water. A stream of water 111, introduced at 4° C., circulated in this absorption column in order to absorb the acrolein. The noncondensable gases mentioned above were discharged 113 at the top of the absorption column and a 6% by weight aqueous acrolein solution 2 is obtained at the column bottom.

Purification of Acrolein

The aqueous acrolein solution was purified according to the purification process of the invention (cf. FIG. 1) using a single distillation column 1 comprising a random packing. This column, maintained at atmospheric pressure, was thus fed 2 with an aqueous solution comprising 6% by weight of acrolein. The temperature at the base of the distillation column was maintained at 105° C. by virtue of a boiler. The top of the column was equipped with a condenser 7 in order to cool to 60° C. the mixture withdrawn at the column top. A condensate 9 and an acrolein-rich gas mixture 12 were obtained at this temperature. The condensate was reintroduced 13 in its entirety at the column top 1. Purified acrolein with a purity of 93% by weight (the remaining 7% being mainly water) was isolated 12 by removing all the acrolein-rich gas mixture 8.

After operating for five weeks, no fouling was observed on the packing of the distillation column 1.

Reaction of MTPA

Purified acrolein 12 in the gaseous form and a stoichiometric amount of liquid MSH are introduced, in the presence of catalyst, into a loop reactor 115 with recirculation of MTPA.

The yield is virtually quantitative. The presence of an amount of water introduced by the acrolein thus purified does not cause any trouble in comparison with acrolein originating from an azeotropic distillation.

It is clearly apparent that the purification process according to the present invention makes it possible to greatly reduce fouling deposits in the distillation column used for the purification of acrolein.

What is claimed is:

1. A continuous process for the manufacture of 3-(methylthio)propionaldehyde, the process comprising:
    (a) subjecting propylene to vapor-phase oxidation using a catalyst, to obtain a crude acrolein-based product;
    (b) removing acids present in the crude acrolein-based product;
    (c) absorbing the crude acrolein-based product with water to obtain an aqueous acrolein solution;
    (d) purifying the aqueous acrolein solution to obtain purified gaseous acrolein by a process comprising:
        introducing the aqueous acrolein solution into a distillation column equipped at its base with at least one boiler and at its top with at least one condenser,
        withdrawing a liquid mixture essentially comprising water at the base of the distillation column,
        withdrawing a gas mixture essentially comprising acrolein and water at the top of the distillation column,
        cooling the gas mixture withdrawn at the top of the distillation column in the condenser, to a temperature which makes it possible to obtain, on the one hand, an aqueous condensate and, on the other hand, an acrolein-rich gas mixture, and
        withdrawing the acrolein-rich gas mixture; and
    (e) reacting the purified gaseous acrolein with methyl mercaptan, to obtain 3-(methylthio)propionaldehyde;
    wherein:
    noncondensable gases produced in step (a) are separated from the acrolein prior to step (e).

2. The process as claimed in claim 1, wherein the noncondensable gases produced in step (a) are separated from the acrolein prior to step (d).

3. The process as claimed in claim 2, wherein the noncondensable gases produced in step (a) are separated from the acrolein prior to step (c).

4. The process as claimed in claim 3, wherein the noncondensable gases produced in step (a) are separated from the acrolein in steps (b) and (c).

5. The process as claimed in claim 1, wherein the noncondensable gases separated from the acrolein are recycled to the vapor-phase oxidation reaction of step (a).

6. The process as claimed in claim 1, wherein the noncondensable gases separated from the acrolein are discharged and incinerated.

7. The process as claimed in claim 1, wherein purified gaseous acrolein is reacted with gaseous methyl mercaptan in step (e).

8. The process as claimed in claim 1, wherein the aqueous acrolein solution has a concentration of acrolein of less than or equal to the solubility limit of acrolein in water.

9. The process as claimed in claim 1, wherein the distillation column is maintained at a pressure P and the temperature in the condenser is maintained at a value T according to $T > 21.28*P + 32.9$.

10. The process as claimed in claim 9, wherein the distillation column is maintained at atmospheric pressure and the temperature in the condenser is maintained at a value of greater than 54° C.

11. The process as claimed in claim 1, wherein the acrolein-rich gas mixture has an acrolein concentration ranging from 86 to 95% by weight.

12. The process as claimed in claim 1, wherein the condensate is at least partially reintroduced into the distillation column.

13. The process as claimed in claim 12, wherein all of the condensate is reintroduced at the top of the distillation column.

14. A continuous process for the manufacture of 3-(methylthio)propionaldehyde, the process comprising:
    (a) subjecting propylene to vapor-phase oxidation using a catalyst, to obtain a crude acrolein-based product;
    (b) removing acids present in the crude acrolein-based product;
    (c) absorbing the crude-acrolein product with water to obtain an aqueous acrolein solution separated from non-condensable gases,
    (d) purifying the aqueous acrolein solution to obtain purified gaseous acrolein by a process comprising:
        introducing the aqueous acrolein solution into a distillation column equipped at its base with at least one boiler and at its top with at least one condenser,
        withdrawing a liquid mixture essentially comprising water at the base of the distillation column,
        withdrawing a gas mixture essentially comprising acrolein and water at the top of the distillation column,
        cooling the gas mixture withdrawn at the top of the distillation column in the condenser, to a temperature which makes it possible to obtain, on the one hand, an aqueous condensate and, on the other hand, an acrolein-rich gas mixture, and
        withdrawing the acrolein-rich gas mixture, and
    (e) reacting the purified gaseous acrolein directly with methyl mercaptan to obtain 3-(methylthio)propionaldehyde.

15. The process as claimed in claim 14, wherein the methyl mercaptan of step (e) is in the gas phase.

16. A process for the purification of acrolein, the process comprising:
    introducing an aqueous acrolein solution into a distillation column equipped at its base with at least one boiler and at its top with at least one condenser,
    withdrawing a liquid mixture comprising water at the base of the distillation column,
    withdrawing a gas mixture comprising acrolein at the top of the distillation column,
    cooling the gas mixture withdrawn at the top of the distillation column in the condenser, to a temperature which makes it possible to obtain, on the one hand, an aqueous condensate and, on the other hand, an acrolein-rich gas mixture, and
    withdrawing the acrolein-rich gas mixture,
    wherein:
    the liquid mixture withdrawn at the base of the distillation column is a nonazeotropic liquid mixture essentially comprising water;
    the aqueous condensate is substantially depleted in acrolein; and
    the acrolein-rich gas mixture is substantially enriched in acrolein.

17. The process as claimed in claim 16, wherein the gas mixture obtained at the distillation column top comprises, by volume, between 30% and 70% of water.

* * * * *